United States Patent
Kurokawa (10) Patent No.: US 10,146,058 B2
(45) Date of Patent: Dec. 4, 2018

(54) VISUAL LINE DIRECTION SENSING DEVICE

(71) Applicant: DENSO CORPORATION, Kariya, Aichi-pref. (JP)

(72) Inventor: Kazumasa Kurokawa, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 184 days.

(21) Appl. No.: 15/035,251

(22) PCT Filed: Oct. 30, 2014

(86) PCT No.: PCT/JP2014/005488
§ 371 (c)(1),
(2) Date: May 9, 2016

(87) PCT Pub. No.: WO2014/072100
PCT Pub. Date: May 21, 2015

(65) Prior Publication Data
US 2016/0291330 A1    Oct. 6, 2016

(30) Foreign Application Priority Data

Nov. 13, 2013  (JP) ................................ 2013-235104

(51) Int. Cl.
*G02B 27/01*        (2006.01)
*A61B 3/113*        (2006.01)
(Continued)

(52) U.S. Cl.
CPC .......... *G02B 27/0179* (2013.01); *A61B 3/113* (2013.01); *A61B 3/14* (2013.01);
(Continued)

(58) Field of Classification Search
CPC ............ G02B 27/0179; G02B 27/0093; G02B 2027/0187; G02B 27/0101;
(Continued)

(56) References Cited

U.S. PATENT DOCUMENTS

| | | | |
|---|---|---|---|
| 2009/0201225 A1* | 8/2009 | Okada .................... | G02B 27/01 345/7 |
| 2013/0194110 A1* | 8/2013 | Kim ....................... | G02B 27/01 340/905 |

FOREIGN PATENT DOCUMENTS

| | | |
|---|---|---|
| JP | H06194564 A | 7/1994 |
| JP | 2000089905 A | 3/2000 |

(Continued)

*Primary Examiner* — Thai Q Tran
*Assistant Examiner* — Nien Yang
(74) *Attorney, Agent, or Firm* — Harness, Dickey & Pierce, P.L.C.

(57) ABSTRACT

A visual line direction sensing device communicably connected with a head-up display device, which projects an image on a screen disposed ahead of a target, includes an image capture unit capturing a target image from a front side of the target, an acquisition unit acquiring adjusted position information indicative of an image projection position by an adjustment unit of the head-up display device, an estimation unit estimating positions of pupils of the target based on the adjusted position information acquired by the acquisition unit, a setup unit setting an inspection range of the target image captured by the image capture unit with reference to the positions of the pupils estimated by the estimation unit, and a calculator calculating a visual line direction of the target based on a status of the pupils included in the inspection range of the target image set by the setup unit.

5 Claims, 6 Drawing Sheets

(51) Int. Cl.
  *G06F 3/01* (2006.01)
  *A61B 3/14* (2006.01)
  *G02B 27/00* (2006.01)

(52) U.S. Cl.
  CPC ......... *G02B 27/0093* (2013.01); *G02B 27/01* (2013.01); *G02B 27/0101* (2013.01); *G02B 27/0149* (2013.01); *G06F 3/013* (2013.01); *G02B 2027/014* (2013.01); *G02B 2027/0138* (2013.01); *G02B 2027/0154* (2013.01); *G02B 2027/0187* (2013.01)

(58) Field of Classification Search
  CPC ........ G02B 27/0149; G02B 2027/0154; G02B 2027/014; G02B 2027/0138; G02B 27/01; G02B 27/00; A61B 3/113; A61B 3/14; G06F 3/013
  USPC .......................................................... 348/78
  See application file for complete search history.

(56) References Cited

FOREIGN PATENT DOCUMENTS

| | | | |
|---|---|---|---|
| JP | 2005075081 A | 3/2005 | |
| JP | 2008155720 A | 7/2008 | |

\* cited by examiner

FIG. 5A  1ST EXAMPLE OF CAMERA ARRANGEMENT

FIG. 5B  2ND EXAMPLE OF CAMERA ARRANGEMENT

FIG. 5C  3RD EXAMPLE OF CAMERA ARRANGEMENT

FIG. 6

VISUAL LINE DIRECTION SENSING DEVICE

CROSS REFERENCE TO RELATED APPLICATIONS

This application is a U.S. National Phase Application under 35 U.S.C. 371 of International Application No. PCT/JP2014/005488 filed on Oct. 30, 2014 and published in Japanese as WO 2015/072100 A1 on May 21, 2015. This application is based on and claims the benefit of priority from Japanese Patent Application No. 2013-235104 filed on Nov. 13, 2013. The entire disclosures of all of the above applications are incorporated herein by reference.

TECHNICAL FIELD

The present disclosure relates to a visual line direction sensing device which detects a visual line direction of a target in coordination with a head-up display device.

BACKGROUND ART

In recent years, an input method of touching a touch panel disposed on a screen is widely used as a human-machine interface (HMI) between a human and a machine such as a mobile terminal or an in-vehicle instrument. The input method based on a touch panel provides improved operational feeling as compared to a conventional input method of operating, for example, switches. However, the input method based on a touch panel is similar to the conventional input method of operating switches in that the hands of a user need to be moved for operating purposes. Hence, the input method based on a touch panel is not good enough to reduce physical burden on the user. Further, the input method based on a touch panel makes it difficult to perform an operation in a situation where both hands of the user are used to drive a vehicle. Under these circumstances, a visual line input technology is proposed, for instance, in Patent Literature 1. The visual line input technology inputs information by detecting the visual line direction of the user and specifying an object selected by the user on the basis of the detected visual line direction. In addition, a technology proposed, for instance, in Patent Literature 2 applies the visual line input technology to a pointing device that coordinates with an image displayed on a head-up display, which presents information ahead of a driver of a vehicle.

A well-known method of detecting the visual line direction includes capturing an image of the pupils of a target with a camera while the pupils of the target are irradiated with infrared light, and estimating the visual line direction on the basis of an image formed by the infrared light reflected from the pupils in the captured image. This method detects the visual line direction by analyzing the status of the target's pupils in image processing. Therefore, a high-resolution image needs to be captured.

However, when detecting the visual line direction of a driver, it is necessary to capture an image of a wide range in order to properly capture the pupils of the driver. This is because the positions of the pupils vary with the physique and posture of the driver. Thus, it is necessary to use a high-performance camera capable of capturing a high-resolution image of a wide range. Besides, a considerably high arithmetic processing capability is required for rapidly processing a high-resolution image of a wide range.

PRIOR ART LITERATURES

Patent Literatures

Patent Literature 1: JP 2000-89905 A
Patent Literature 2: JP 2005-75081 A

SUMMARY OF INVENTION

The present disclosure has been made in view of the above circumstances. An object of the present disclosure is to provide a visual line direction sensing device that detects a visual line direction of a target by narrowing down an inspection range in coordination with a head-up display displaying an image to the target.

According to an aspect of the present disclosure, a visual line direction sensing device communicably connected with a head-up display device includes an image capture unit, an acquisition unit, an estimation unit, a setup unit, and a calculator. The head-up display device projects an image on a screen disposed ahead of a target and displays the image to the target. The image capture unit captures, from a front side of the target, an image of the target as a target image. The acquisition unit acquires adjusted position information. An adjustment unit included in the head-up display device adjusts an image projection position in accordance with the target and outputs the adjusted position information indicative of an adjusted projection position of the image. The estimation unit estimates positions of pupils of the target based on the adjusted position information acquired by the acquisition unit. The setup unit sets an inspection range in the target image captured by the image capture unit with reference to the positions of the pupils estimated by the estimation unit. The calculator calculates a visual line direction of the target based on a status of the pupils included in the inspection range of the target image set by the setup unit.

According to the above visual line direction sensing device, the visual line direction can be detected by narrowing down the inspection range. The narrowing down of the inspection range is carried out in coordination with the result of image projection position adjustment in the head-up display device. More specifically, the image projection position is optimally adjusted in the head-up display device so as to provide improved viewability to the user. It is estimated that the improved viewability should satisfy a particular positional relationship between the image projection position and the positions of the user's pupils. Thus, with the present disclosure, it is possible to estimate the positions of the target's pupils by using the result of image projection position adjustment in the head-up display device. In the above visual line direction sensing device, after the inspection range is narrowed down with reference to the estimated positions of the pupils, the visual line direction of the target is detected. In this manner, the target's pupils can be properly captured without capturing a wide-range image of the target. This makes it possible to reduce the image capture range of a camera and lessen the burden on the image processing of the target's image.

According to another aspect of the present disclosure, a visual line direction sensing device, which is communicably connected with a head-up display device, includes an image capture unit and a calculator. The head-up display device projects an image on a screen disposed ahead of a target and displays the image to the target. The image capture unit captures, from a front side of the target, an image of the target as a target image. The image capture unit is attached integrally to an image generation unit included in the head-up display device and is disposed at a position which enables an image capturing of the target using an optical path through which an image generated by the image generation unit is projected on the screen. The image generation unit is moved by an adjustment unit to adjust an image projection position in accordance with the target, and the image capture unit moves together with the image generation unit and a position of an image capture range of the image capture unit changes corresponding to a movement of the image capture unit. The calculator calculates a visual line direction based on a status of pupils included in the target image captured under a condition that the position of the image capture range of the image capture unit is adjusted together with an adjustment of the image projection position of the image generation unit by the adjustment unit.

According to the above visual line direction sensing device, the position of the image capture range of the image capture unit is accurately adjusted corresponding to the positions of the pupils of the target in coordination with optimal adjustment of the image projection position that is made in the head-up display device to provide improved viewability to the target. The visual line direction of the target can then be detected on the basis of the target's image that is acquired after the position of the image capture range is adjusted for the positions of the target's pupils. In this manner, the target's pupils can be properly captured without capturing a wide-range image of the target. This makes it possible to reduce the image capture range of a camera and lessen the burden on the image processing of the target's image.

BRIEF DESCRIPTION OF DRAWINGS

The above and other objects, features, and advantages of the present disclosure will become more apparent from the following detailed description made with reference to the accompanying drawings. In the drawings.

EMBODIMENTS FOR CARRYING OUT INVENTION

Embodiments of the present disclosure will now be described with reference to the accompanying drawings.

The present disclosure is not limited to the embodiments described below, and can also be implemented by various other embodiments.

First Embodiment

Description of Configuration of in-Vehicle Display System

An in-vehicle display system to which a visual line direction sensing device according to the present disclosure is applied is an in-vehicle instrument that is capable of operating a head-up display to project an image ahead of a driver of a vehicle. The in-vehicle display system also inputs information using a visual line input interface which coordinates with the image of head-up display. As exemplified in FIGS. 1A and 1B, the in-vehicle display system according to a first embodiment includes, for example, a visual line image calculation device 10, a head-up display (HUD) 20 connected to the visual line image calculation device 10, a camera 30, and a camera drive unit 32.

Figure 1A:
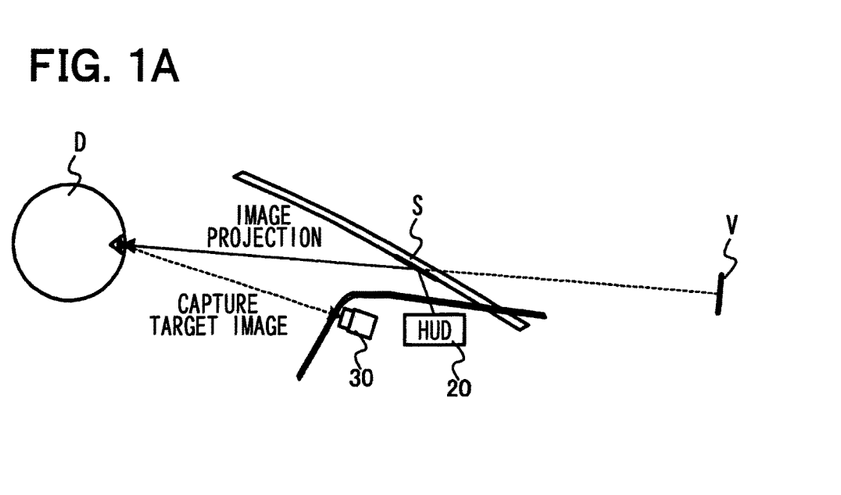
FIG. 1A is a diagram illustrating an in-vehicle display system according to the present disclosure.
Figure 1B:
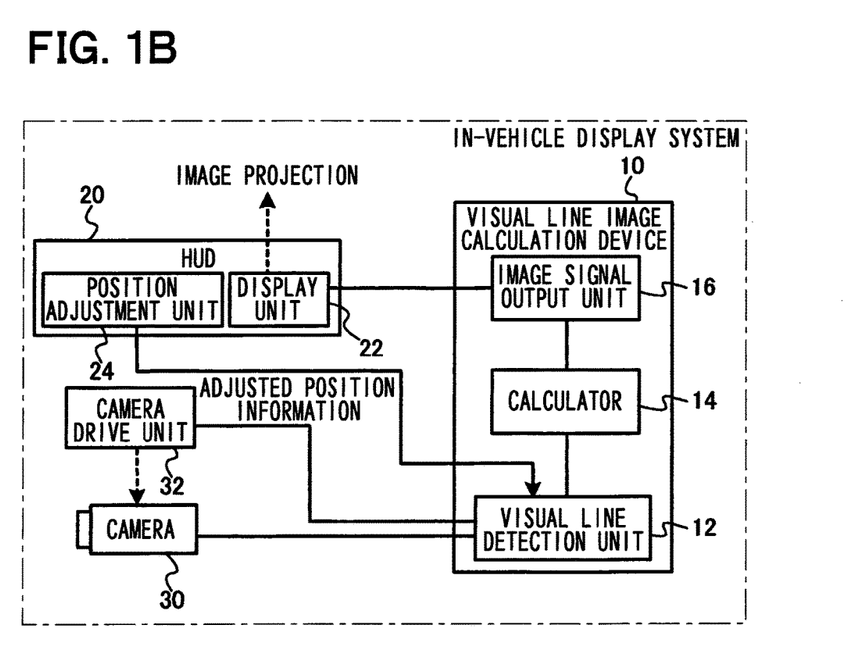
FIG. 1B is a block diagram illustrating a configuration of the in-vehicle display system according to a first embodiment of the present disclosure.

The head-up display 20 is mounted, for example, on a dashboard in front of a driver's seat of the vehicle and used to project an image onto a screen S that is provided by a windshield or of a combiner and disposed in front of the driver. The projected image is reflected on the screen S and viewed by the driver D. The image viewed by the driver D is recognized as a virtual image V formed in the driver's field of view. The virtual image V is generated at a position ahead of the screen S with respect to the driver. The head-up display 20 mainly includes a display unit 22 and a position adjustment unit 24.

The display unit 22 is provided by an optical system that includes, for example, a liquid-crystal panel and a reflecting mirror. The liquid-crystal panel outputs an image based on an image signal outputted from the visual line image calculation device 10. The reflecting mirror projects the outputted image onto the screen S. The position adjustment unit 24 is an actuator that adjusts the position of the image projected onto the screen S by changing the position and angle of the image display surface of the display unit 22 or the optical system to vary the direction of image projection.

When the positions of pupils vary with the physique and posture of individual driver D, the position at which the image projected by the head-up display 20 is visible varies accordingly. Therefore, the position adjustment unit 24 is capable of correcting an image projection position in such a manner that the virtual image V is visible at an appropriate position relative to the positions of the pupils of the driver D. The position adjustment unit 24 may be designed, for example, to coordinate with a power seat of the vehicle and automatically adjust an image display position on the basis of a setting preregistered for individual driver D. Alternatively, the position adjustment unit 24 may adjust the image display position on the basis of an operation performed by the driver D.

The visual line image calculation device 10 is mainly provided by a microcomputer that includes a visual line detection unit 12, a calculator 14, and an image signal output unit 16. The visual line detection unit 12 specifies the visual line direction of the driver D, which is a target, by processing an image captured by the camera 30. In this instance, the visual line detection unit 12 estimates the positions of the pupils of the driver D on the basis of adjusted-position information acquired from the position adjustment unit 24. The visual line detection unit 12 then adjusts the image capture range of the camera 30 on the basis of the estimated positions of the pupils and performs image processing to specify the visual line direction. A series of these processes will be described in detail later.

The calculator 14 receives an image inputted from an in-vehicle instrument (not shown) connected to the visual line image calculation device 10 and outputs the inputted image to the image signal output unit 16, and the image signal output unit 16 outputs the image as an image signal. The in-vehicle instrument executes an application that draws an image to be displayed on the head-up display 20. Further, based on the visual line direction of the driver D, which is outputted from the visual line detection unit 12, the calculator 14 specifies the position of an image watched by the driver D. The calculator 14 then outputs information indicative of the specified image position to the in-vehicle instrument. The image signal output unit 16 outputs the image inputted from the calculator 14 to the head-up display 20 as an image signal.

The camera 30 is disposed on the dashboard in front of the driver's seat of the vehicle and captures an image of a region around the face of the driver D sitting on the driver's seat. The position and orientation of the camera 30 can be varied to change the position of the image capture range on the assumption that the positions of the pupils vary with the physique and posture of the driver D, which is the target. The camera drive unit 32 is an actuator that changes the position of the image capture range of the camera 30 by changing the position and orientation of the camera 30 under control of the visual line detection unit 12. Consequently, the pupils of the driver D can be properly captured within the image capture range by changing the position of the image capture range of the camera 30 on the basis of the positions of the pupils of the driver D.

Description of Visual Line Detection Process (First Embodiment)

The steps of a visual line detection process (first embodiment) performed by the visual line detection unit 12 will now be described with reference to the flowchart of FIG. 2.

In S100, the position adjustment unit 24 of the head-up display 20 adjusts the image projection position of the display unit 22. In S102, the visual line detection unit 12 acquires the adjusted position information indicative of the result of image projection position adjustment by the position adjustment unit 24. The adjusted-position information includes, for example, information indicative of correction values for the image projection position and image projection angle. Then, in S104, the visual line detection unit 12 calculates the positions of the pupils of the target (driver D) on the basis of the adjusted position information acquired in S102.

Next, in S106, the visual line detection unit 12 moves the camera 30 on the basis of the positions of the pupils of the target, which was calculated in S104 so that the image capture range of the camera 30 is adjusted for the positions of the target's pupils. More specifically, the visual line detection unit 12 operates the camera drive unit 32 on the basis of parameters, which predefine the relationship between the positions of the target's pupils and the orientation and position of the camera, in order to adjust the orientation and position of the camera 30 so that the target's pupils are positioned within the image capture range of the camera 30. Then, in S108, the visual line detection unit 12 calculates the visual line direction of the target on the basis of an image of the target that is captured by the camera 30 whose image capture range is adjusted. In this instance, the target's image is processed by using a predetermined algorithm in order to analyze the status of the pupils shown in the image and calculate the visual line direction.

Modification of First Embodiment

The visual line detection process according to the first embodiment has been described on the assumption that the position of the image capture range of the camera 30 is adjusted by moving the camera 30 on the basis of the calculated positions of the target's pupils. In another example, a partial region may be cut out corresponding to the positions of the target's pupils from the target's image captured by the camera 30 on the basis of the calculated positions of the target's pupils, and calculate the visual line direction of the target from an image of the cut-out region. In this instance, the target's image is captured while the camera 30 is oriented in a predetermined direction, and the camera drive unit 32 is eliminated from the in-vehicle display system.

Figure 2:
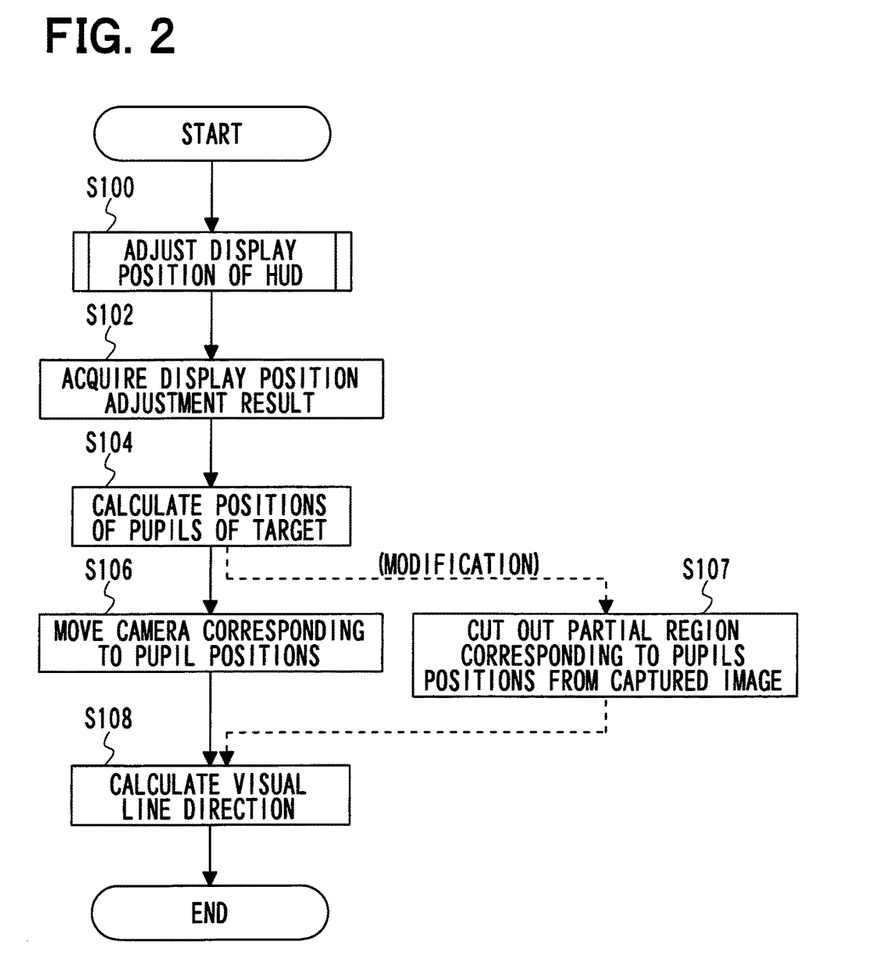
FIG. 2 is a flowchart illustrating the steps of a visual line detection process according to the first embodiment of the present disclosure.

More specifically, the visual line detection unit 12 performs S107 in place of S106 in the above-described visual line detection process (see FIG. 2). In S107, the visual line detection unit 12 cuts out a region of a predetermined size, which corresponds to the positions of the target's pupils specified in S104, from the target's image captured by the camera 30.

Figure 3A:
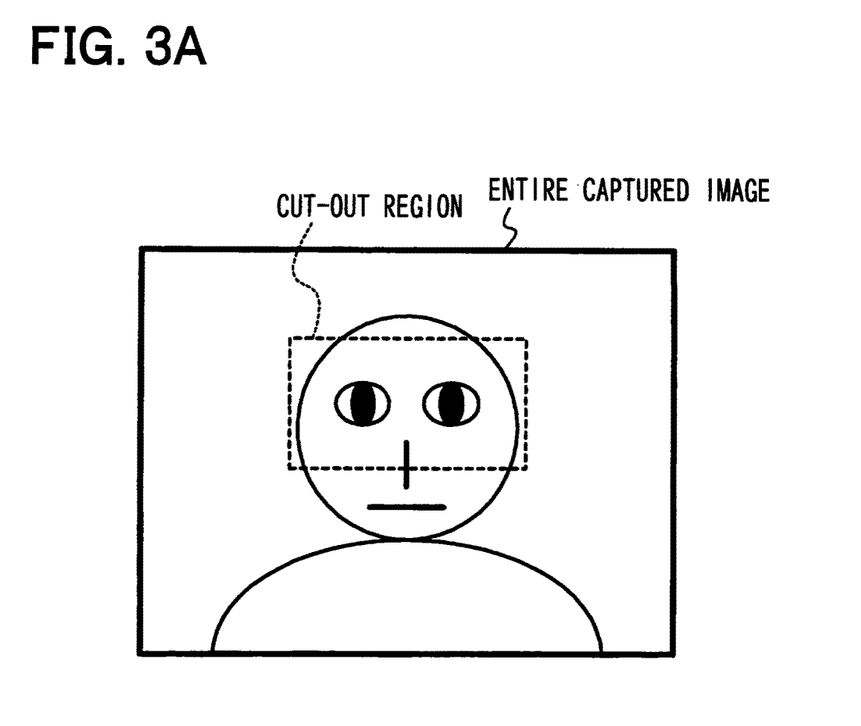
FIG. 3A is a diagram illustrating a case where an inspection target image is to be cut out.

For example, the position of the cut-out region is specified on the basis of parameters that predefine the relationship between the calculated positions of the target's pupils and the positions of the pupils shown in the image captured by the camera 30. Based on an estimated distance between the camera 30 and the face of the target sitting in the driver's seat of the vehicle, a size of the cut-out region is determined to include both eyes of the target and a region around the eyes. A partial image corresponding to the cut-out region is then cut out as an inspection target image from the entire image captured by the camera 30 as exemplified in FIGS. 3A and 3B.

Figure 3B:
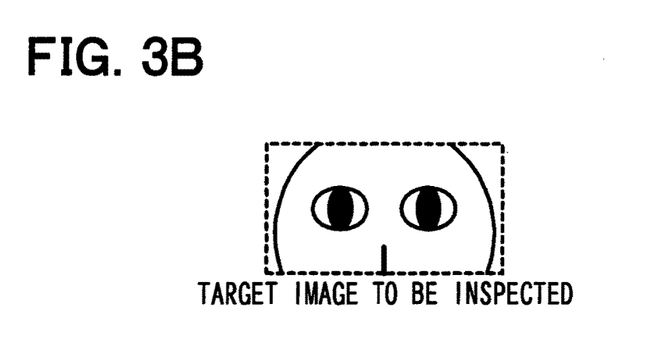
FIG. 3B is a diagram illustrating a region that is cut out from an entire captured image shown in FIG. 3A as the inspection target image.

Then, in S108, the visual line detection unit 12 processes the inspection target image cut out in S107 by using a predetermined algorithm in order to calculate the visual line direction on the basis of the status of the pupils shown in the inspection target image.

In the present embodiment, the camera 30 corresponds to an image capture unit, the display unit 22 corresponds to an image generation unit, the position adjustment unit 24 corresponds to an adjustment unit, a process performed in S102 by the visual line detection unit 12 corresponds to an acquisition unit, a process performed in S104 by the visual line detection unit 12 corresponds to an estimation unit, the visual line detection unit 12 corresponds to a setup unit, a process performed in S108 by the visual line detection unit 12 corresponds to a calculator, and the camera drive unit 32 corresponds to a drive unit.

Advantageous Effects

The in-vehicle display system according to the first embodiment provides the following advantageous effects.

The visual line direction can be detected after the inspection range is narrowed down in coordination with the result of image projection position adjustment by the position adjustment unit 24 of the head-up display 20. In the first embodiment, the image projection position is optimally adjusted in the head-up display 20 so as to provide improved viewability to the target. This makes it possible to estimate the positions of the target's pupils by using the result of the adjustment performed in the head-up display 20. Thus, the inspection range can be narrowed down by repositioning the camera 30 to move the image capture range or cutting out a partial region from the captured image on the basis of the estimated positions of the pupils. As a result, it is possible to reduce the image capture range of the camera and lessen the burden on the image processing of the target's image.

Second Embodiment

Description of Configuration of in-Vehicle Display System

Figure 4A:
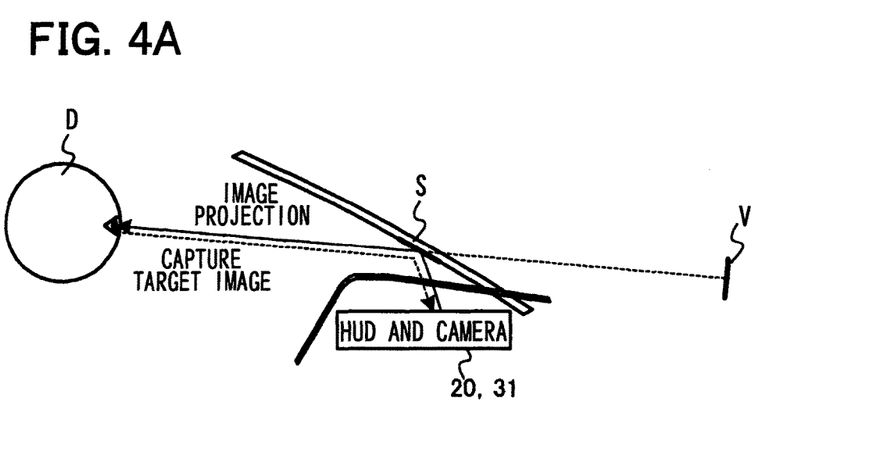
FIG. 4A is a diagram illustrating an in-vehicle display system according to the present disclosure.
Figure 4B:
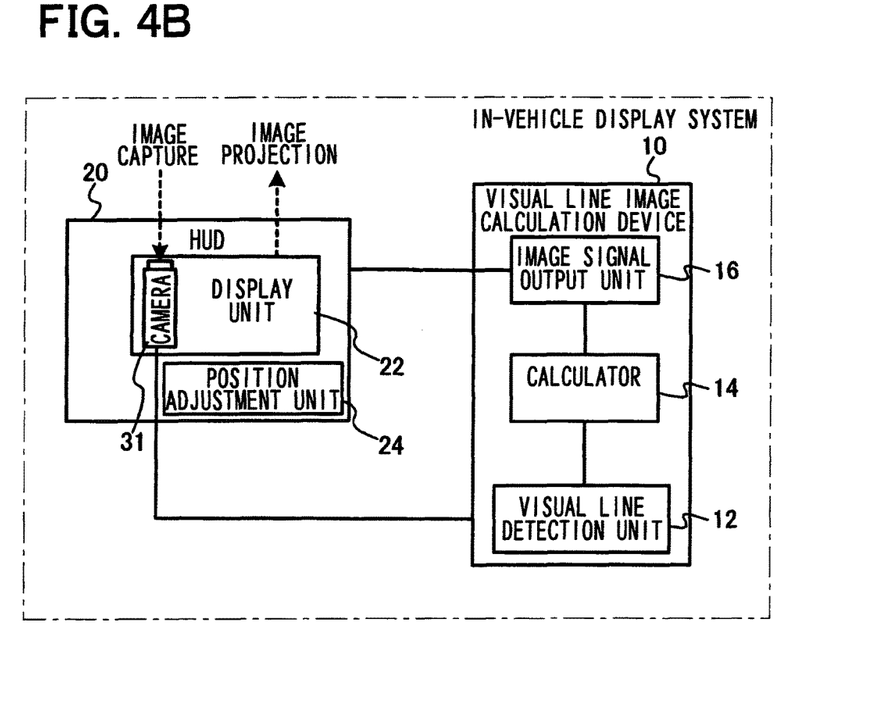
FIG. 4B is a block diagram illustrating a configuration of the in-vehicle display system according to a second embodiment of the present disclosure.

As exemplified in FIGS. 4A and 4B, the in-vehicle display system according to a second embodiment includes, for example, a visual line image calculation device 10, a head-up display device (HUD) 20 connected to the visual line image calculation device 10, and a camera 31. The second embodiment differs from the first embodiment in that the camera 31, which captures an image of the driver D, that is, the target, is mounted integrally with a display unit 22 included in the head-up display 20. In FIGS. 4A and 4B, elements identical with those in the first embodiment are designated by the same reference numerals as their counterparts and will not be redundantly described.

The camera 31 is mounted in such a manner as to capture an image of a region near the pupils of the driver D, which is the target, through an optical path through which an image output from the display unit 22 of the head-up display 20 is projected onto a screen S. This ensures that the image projected from the display unit 22 is reflected on the screen S and viewed by the driver D, and that the image of the region near the pupils of the driver D is reflected on the screen S and captured by the camera 31.

Further, the camera 31 is mounted on a part that moves when the direction of image projection by the display unit 22 is adjusted by a position adjustment unit 24. This ensures that the image projection position of the display unit 22 and the position of the image capture range of the camera 31 are moved together by the position adjustment unit 24. In other words, when the image projection position is adjusted so that the image projected from the display unit 22 is displayed at an appropriate position as viewed from the driver D, the camera 31 is oriented in such a direction that the pupils of the driver D are positioned within the image capture range of the camera 31.

A plurality of concrete examples of a structure in which the camera 31 is disposed on the display unit 22 will now be described with reference to FIGS. 5A, 5B, and 5C. It is assumed that the display unit 22 includes a liquid-crystal panel 26 (for example, a TFT LCD) and a backlight 28. The liquid-crystal panel 26 forms an image pattern by varying the transmittance of light. The backlight 28 is a light source that illuminates the back surface of the liquid crystal panel 26 with light to display the image pattern as an image.

Figure 5A:
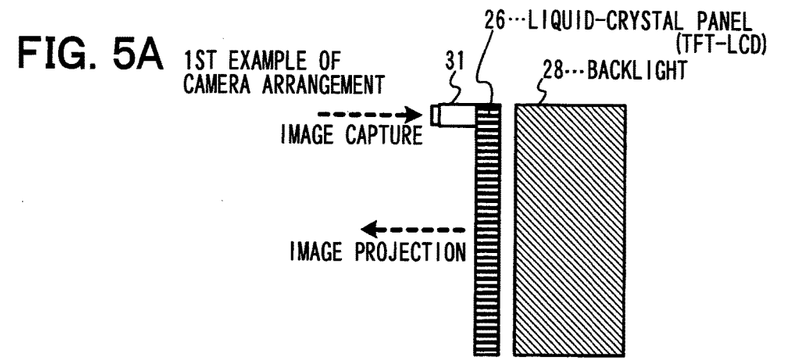
FIGS. 5A to 5C are diagrams illustrating examples of camera installation.

In the case of FIG. 5A, the camera 31 is disposed in the vicinity of the display surface of the liquid-crystal panel 26. In this case, the central direction of the image capture range of the camera 31 is in parallel with the direction of image projection by the liquid-crystal panel 26 and the backlight 28. In this example, the camera 31 is disposed on an outer edge of the liquid-crystal panel 26 in order not to obstruct an image display operation of the liquid-crystal display 26.

Figure 5B:
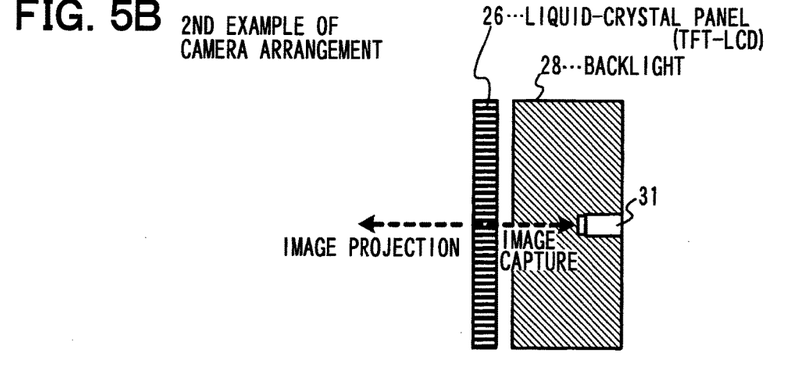

In the case of FIG. 5B, the camera 31 is disposed in the vicinity of the rear surface of the liquid-crystal panel 26. In this case, the central direction of the image capture range of the camera 31 is in parallel with the direction of image projection by the liquid-crystal panel 26 and the backlight 28. Further, the image display operation of the liquid-crystal display 26 is not obstructed because the camera 31 is disposed on the rear surface side of the liquid-crystal panel 26. Therefore, the camera 31 can be disposed at the center of the liquid-crystal panel 26. While the liquid-crystal panel 26 is operating to allow light to be transmitted through the liquid-crystal panel 26, the camera 31 is capable of capturing an image of the target through the liquid-crystal panel 26.

Figure 5C:
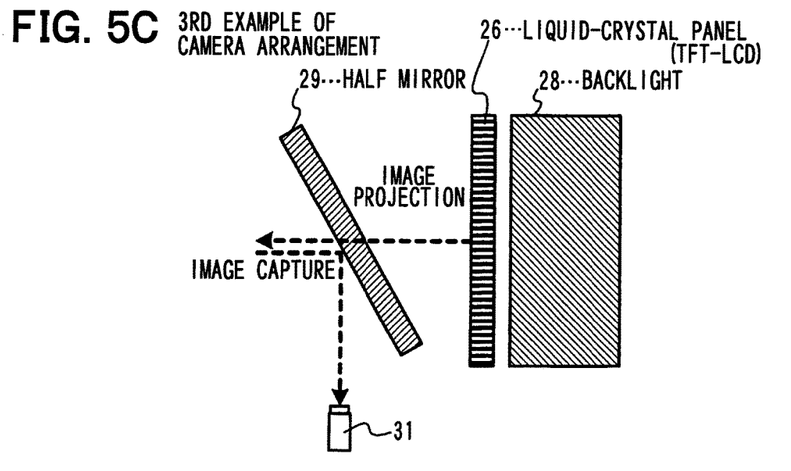

In the case of FIG. 5C, a half mirror 29 is disposed on an optical path through which an image is projected by the liquid-crystal panel 26 and the backlight 28. The camera 31 is positioned so that light coming from the direction of image projection is reflected by the half mirror 29. In this case, the image displayed by the liquid-crystal panel 26 and the backlight 28 is transmitted through the half mirror 29 and projected onto the screen S. Meanwhile, an image of the target, which is reflected on the screen S and incident on the display unit 22, is further reflected by the half mirror 29 and captured by the camera 31.

Description of Visual Line Detection Process (Second Embodiment)

Figure 6:
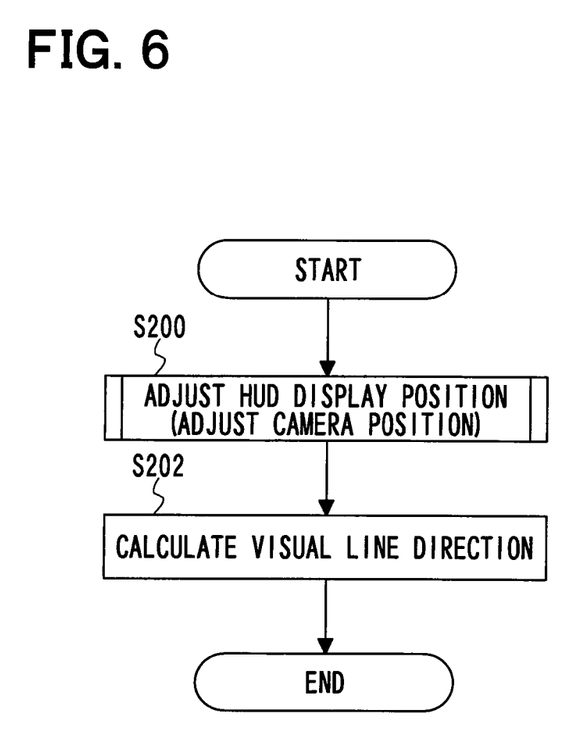
FIG. 6 is a flowchart illustrating the steps of the visual line direction detection process according to the second embodiment of the present disclosure.

The steps of the visual line detection process (second embodiment) performed by the visual line detection unit 12 will now be described with reference to the flowchart of FIG. 6.

In S200, the position adjustment unit 24 of the head-up display 20 adjusts the image projection position of the display unit 22. In this instance, the position adjustment unit 24 adjusts not only the position of image projection by the display unit 22, but also adjusts the position of the image capture range of the camera 31. Then, in S202, the visual line detection unit 12 calculates the visual line direction of the target on the basis of an image of the target that is captured by the camera 31 whose image capture range is adjusted. In this instance, the target's image is processed by using a predetermined algorithm in order to analyze the status of the pupils shown in the image and calculate the visual line direction.

In the present embodiment, the camera 31 corresponds to the image capture unit, the display unit 22 corresponds to the image generation unit, the position adjustment unit 24 corresponds to the adjustment unit, and a process performed in S202 by the visual line detection unit 12 corresponds to the calculator.

Advantages

The in-vehicle display system according to the second embodiment provides the following advantages.

The position of the image capture range of the camera 31 disposed integrally with the display unit 22 is accurately adjusted for the positions of the target's pupils in coordination with optimal adjustment of the image projection position that is made in the head-up display 20 to provide improved viewability to the target. The visual line direction of the target can then be detected on the basis of an image that is acquired after the position of the image capture range is adjusted for the positions of the target's pupils. In this manner, the target's pupils can be properly captured without capturing a wide-range image of the target. This makes it possible to reduce the image capture range of a camera used to capture an image of the target and lessen the burden on the image processing of the target's image.

It is noted that a flowchart or the processing of the flowchart in the present disclosure includes sections (also referred to as steps), each of which is represented, for instance, as S100. Further, each section can be divided into several sub-sections while several sections can be combined into a single section. Furthermore, each of thus configured sections can be also referred to as a circuit, device, module, or means.

Each or any combination of sections explained in the above can be achieved as (i) a software section in combination with a hardware unit (e.g., computer) or (ii) a hardware section, including or not including a function of a related apparatus; furthermore, the hardware section (e.g., integrated circuit, hard-wired logic circuit) may be constructed inside of a microcomputer.

While the present disclosure has been described in conjunction with the foregoing embodiments, it is to be understood that the present disclosure is not limited to the foregoing embodiments and the structures of the foregoing embodiments. The present disclosure is intended to cover various exemplary modifications and equivalent modifications. In addition, various combinations and configurations and other combinations and configurations that additionally include only one element or more than one element or include a smaller number of elements are also within the spirit and scope of the present disclosure.

What is claimed is:

1. A visual line direction sensing device communicably connected with a head-up display device, wherein the head-up display device projects an image on a screen disposed ahead of a target and displays the image to the target, the visual line direction sensing device comprising:
   an image capturer capturing, from a front side of the target, an image of the target as a target image; and
   a microcomputer connected to the image capturer, the microcomputer configured to include:
      an acquirer acquiring adjusted position information;
      an adjuster included in the head-up display device, the adjuster adjusting an image projection position in accordance with the target and outputting the adjusted position information indicative of an adjusted projection position of the image,
         the adjuster automatically adjusting an image display position based on one of a setting preregistered for a driver, or an operation performed by the driver,
         the adjuster coordinating with a power seat of a vehicle when the adjuster automatically adjusts the image display position, and
         the adjusted position information including information indicative of a correction value of the image projection position and a correction value of an image projection angle;
      an estimator estimating positions of pupils of the target based on the adjusted position information acquired by the acquirer;
      a setter setting an inspection range in the target image captured by the image capturer with reference to the positions of the pupils estimated by the estimator; and
      a calculator calculating a visual line direction of the target based on a status of the pupils included in the inspection range of the target image set by the setter, wherein
   the setter cuts out a partial region corresponding to the positions of the pupils estimated by the estimator from the target image, and setting the partial region as the inspection range, and
   the calculator calculates the visual line direction based on the status of the pupils included in the partial region of the target image cut out by the setter.

2. The visual line direction sensing device according to claim 1, further comprising:
   a driver changing a position of an image capture range of the image capturer by moving an orientation of the image capturer, wherein
   the setter controls the driver to adjust the position of the image capture range of the image capturer so that the positions of the pupils estimated by the estimator are included in the image capture range of the image capturer as the inspection range, and
   the calculator calculates the visual line direction based on the status of the pupils included in the inspection range of the target image that is captured after the position of the image capture range of the image capturer is adjusted by the setter.

3. The visual line direction sensing device according to claim 1, wherein
   the image capturer is disposed on a side of a display surface of an image create or which creates an image pattern in an image generator.

4. The visual line direction sensing device according to claim 1, wherein
   the image capturer is disposed on an opposite side of a display surface of an image create or which creates an image pattern in the image generator.

5. The visual line direction sensing device according to claim 1, wherein
   a half mirror is disposed on the optical path through which the image generated by the image generator is projected on the screen and the image capturer is disposed at a position which enables a capturing of the target image reflected by the half mirror.

\* \* \* \* \*